United States Patent [19]
Harandi et al.

[11] Patent Number: 5,208,387
[45] Date of Patent: May 4, 1993

[54] TWO STAGE PROCESS FOR PRODUCTION OF DIISOPROPYL ETHER

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 813,716

[22] Filed: Dec. 27, 1991

[51] Int. Cl.$^5$ .................. C07C 41/09; C07C 41/05
[52] U.S. Cl. .................................. 568/695; 518/197
[58] Field of Search .......................... 568/695, 697

[56] References Cited

U.S. PATENT DOCUMENTS

| | | |
|---|---|---|
| 4,857,664 | 8/1989 | Huang et al. |
| 4,886,918 | 12/1989 | Sorensen et al. |
| 4,906,787 | 3/1990 | Huang et al. |
| 4,927,977 | 5/1990 | Child et al. |
| 4,935,552 | 6/1990 | Child et al. |
| 4,967,020 | 10/1990 | Marler et al. |

*Primary Examiner*—Howard T. Mars
*Attorney, Agent, or Firm*—Alexander J. McKillop; Malcolm D. Keen; L. G. Wise

[57] ABSTRACT

An improved process is disclosed for the acid catalyzed production of DIPE from propene and water feedstreams that eliminates the propene recycle stream to the olefin hydration reactor and achieves high propene conversion. The accomplishment is achieved by carrying out the hydration and etherification reactions in two stages wherein the first stage comprises a zeolite catalyzed hydration and etherification of propene employing a minimum of water feed. The second stage converts unconverted propene from the first stage reactor by hydration and etherification to DIPE in contact with an acidic catalyst, preferably acidic resin, and an excess of water. Isopropanol (IPA) from both the first and second stage reactor is recovered as an aqueous azeotrope by a combination of distillation and extraction steps and the azeotrope is recycled to the first stage reactor. In this way, IPA rather than propene is recycled and the advantageous capabilities of the first stage zeolite catalyst for IPA etherification to DIPE are more fully utilized in that reactor.

20 Claims, 1 Drawing Sheet

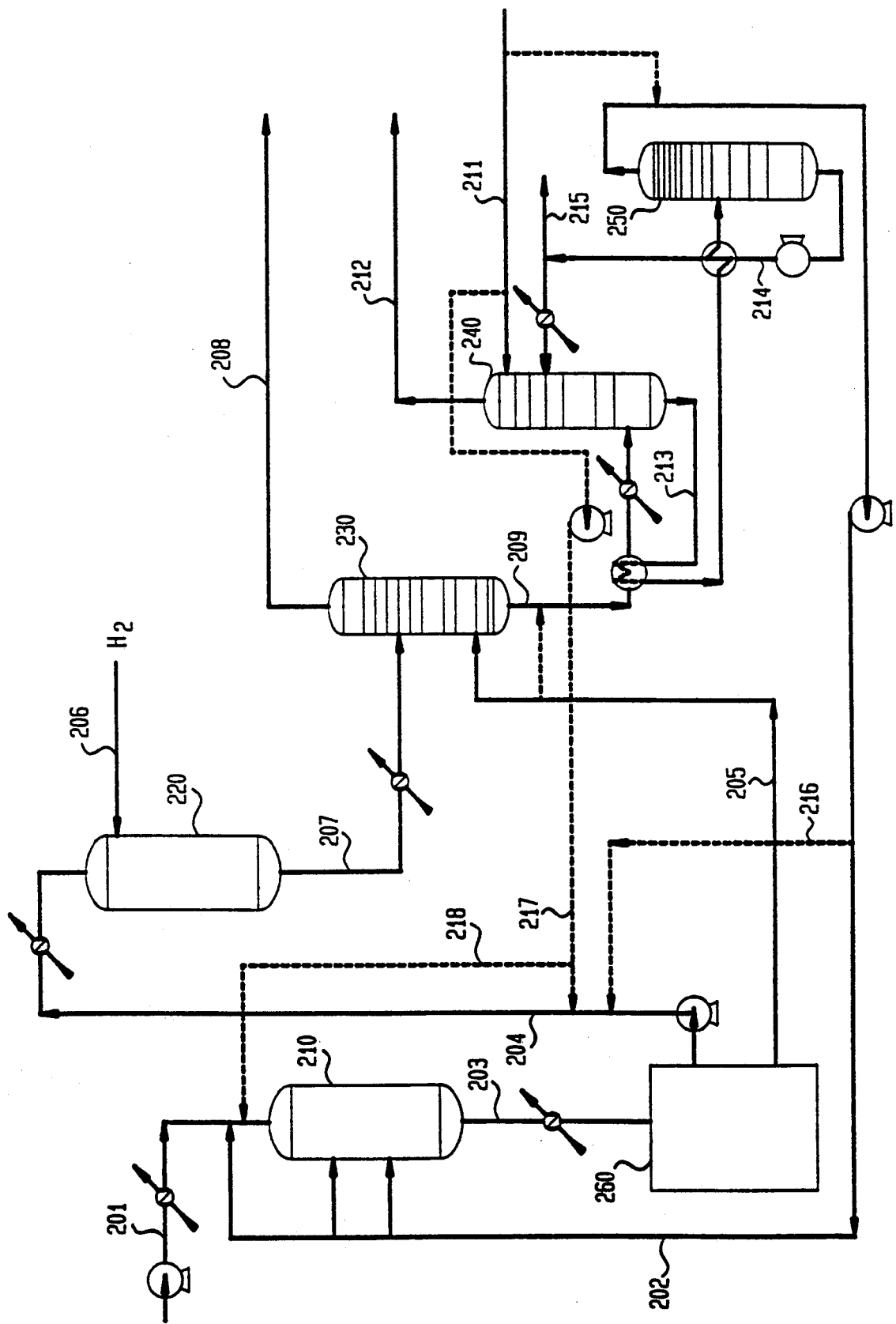

TWO STAGE PROCESS FOR PRODUCTION OF DIISOPROPYL ETHER

This invention relates to an improved process employing once through propene feed for the production of high octane value diisopropyl ether (DIPE). More particularly, the invention relates to improvements in the DIPE process that eliminates the requirement for recycling unconverted propene to the olefin hydration and etherification zone while maintaining high per pass conversion of propene to DIPE.

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels.

The catalytic hydration of olefins, particularly $C_3$ and $C_4$ olefins, to provide alcohols and ethers is a well-established art. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others. U.S. Pat. No. 4,886,918 to Sorensen et al. disclosing olefin hydration and etherification to produce DIPE and isopropanol (IPA) is incorporated herein by reference.

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

The production of ether from secondary alcohols such as isopropanol and light olefins is known. As disclosed in U.S. Pat. No. 4,182,914, DIPE is produced from IPA and propylene in a series of operations employing a strongly acidic cationic exchange resin as catalyst. Recently, processes for the hydration of olefins to provide alcohols and ethers using zeolite catalyst such as ZSM-5 or zeolite Beta have been disclosed in U.S. Pat. Nos. 4,214,107 and 4,499,313 to Bell et al.; and U.S. Pat. Nos. 4,757,664, 4,857,664 and 4,906,187 to T. Huang. These patents are incorporated herein in their entirety by reference.

In the conversion of a water feedstream and a $C_3$ hydrocarbons feedstream comprising propene and propane to DIPE and IPA as conventionally practiced, the conversion per pass is about 60%. The reaction effluent is a mixture containing unreacted water, $C_3$ hydrocarbons and hydrocarbon oligomeric by-products, in addition to the DIPE and IPA products. Separating these components requires multiple distillation and extraction operations that represent a substantial part of the overall process costs. $C_3$ and any lower hydrocarbons present are effectively removed by distillation and propene is recycled to the high pressure hydration and etherification zone. However, separation of DIPE and IPA is accomplished by an aqueous extraction operation that requires a further distillation step to separate water and IPA/water azeotrope.

The need to separate and recycle propene to the high pressure DIPE reaction zone imposes severe economic burdens on the overall DIPE process, particularly due to the cost associated with splitting the $C_3$ recycle stream containing unconverted propene. While it is known that zeolite catalyst such as zeolite Beta can achieve very high per pass conversion of propene to DIPE and, theoretically at least, sharply reduce propene recycle, that achievement results in unacceptably high rates for catalyst deactivation. High mol ratios of water to propene are required for the acidic zeolite catalyzed hydration step to achieve high propene conversion to IPA. Under reaction conditions, these levels of excess water result in a hydrothermal attack on zeolite and more rapid catalyst deactivation. Thus, zeolite's advantage vis-a-vis high propene conversion to DIPE are sharply compromised by a more rapid catalyst deactivation in the presence of the large excesses of water required for high propene conversion in the hydration step of the overall reaction.

It is an object of the present invention to provide a process for the production of DIPE having lower operating cost and capital cost.

A further object of the present invention is to provide a process for DIPE production with high propene conversion without recycling unconverted propene.

Another object of the present invention is to provide a once through process, based on propene, for DIPE production at high propene conversion employing zeolite catalyst.

SUMMARY OF THE INVENTION

An improved process has been discovered for the acid catalyzed production of DIPE from propene and water feedstreams that eliminates the propene recycle stream to the olefin hydration reactor and achieves high propene conversion. The accomplishment is achieved by carrying out the hydration and etherification reactions in two stages wherein the first stage comprises a zeolite catalyzed hydration and etherification of propene employing a low excess of water. The second stage converts unconverted propene from the first stage reactor by hydration and etherification to DIPE in contact with an acidic catalyst, preferably acidic resin, and a relatively high excess of water. Isopropanol (IPA) from both the first and second stage reactor is recovered by a combination of distillation and extraction steps and is recycled to the first stage reactor. In this way, IPA rather than propene is recycled and the advantageous capabilities of the first stage zeolite catalyst for IPA etherification to DIPE are more fully utilized in that reactor.

More particularly, a process is disclosed for the production of high octane value diisopropyl ether without recycling unconverted propene which comprises contacting $C_3$ hydrocarbon feedstock containing propene and a recycle stream comprising isopropanol and water with acidic shape selective metallosilicate catalyst particles in a first fixed bed reactor under olefin hydration and etherification conditions whereby a first reactor effluent stream is produced comprising diisopropyl ether, isopropanol, unconverted propene and water. The effluent from the first reactor is separated and a first fraction rich in unconverted propene and a second fraction rich in diisopropyl ether and isopropanol is recovered. The foregoing first fraction and excess water are introduced into a second fixed bed reactor under olefin hydration and etherification conditions in contact with acidic etherification and hydration catalyst particles whereby a second reactor effluent stream is produced comprising diisopropyl ether, isopropanol, unconverted $C_3$ hydrocarbons and water. The foregoing second fraction and the second reactor effluent stream are separated whereby a stream comprising high octane diisopropyl ether and a stream comprising isopropanol and water are produced as well as a stream comprising water. A portion of the isopropanol and water stream is recycled to the first reactor.

The invention includes an improvement wherein, in the process for the production of diisopropyl ether comprising contacting a $C_3$ hydrocarbon feedstock containing propene and fresh water with shape selective metallosilicate catalyst particles in at least one fixed bed reactor under olefin hydration and etherification conditions, an improvement is achieved comprising:

contacting said propene sequentially in a first reactor containing said metallosilicate catalyst under olefin hydration and etherification conditions with a recycle stream comprising isopropanol and water;

contacting unconverted propene from said first reactor with excess water in a second reactor containing acidic olefin hydration and etherification catalyst under olefin hydration and etherification conditions; and separating effluent from said first and second reactor to remove water and unconverted hydrocarbon streams, recover diisopropyl ether and provide said recycle stream.

DESCRIPTION OF THE FIGURES

The FIGURE is a schematic representation of the DIPE process of the present invention.

DETAILED DESCRIPTION OF THE INVENTION

In the process to prepare DIPE a feedstock comprising propene or a refinery $C_3$ hydrocarbon stream comprising olefins and paraffins, i.e., propene and propane, is contacted at elevated pressure with an acidic catalyst and water as a reactant to hydrate propene to form isopropanol (IPA) and DIPE. Minor amounts of oligomerization products of propene are also formed in the acidic catalyst environment, particularly hexenes and nonenes. On a per pass basis, the conversion of propene generally is about 60%, or between 50% and 70%. The effluent from the hydration and etherification zone is conventionally passed to a fractionator wherein a bottom stream is separated containing IPA and DIPE and an overhead stream that contains the unreacted $C_3$ hydrocarbons comprising propene and propane, if an olefin and paraffin feedstock has been used. The $C_3$ stream, typically containing both propene and propane, can be recompressed and recycled to the pressurized DIPE reactor. Since the recycle stream is rich in propane the DIPE feedstock stream pressure is increased in order to maintain the partial pressure of propene in the reactor. To avoid this, the recycle stream may be fractionated to purify propene recycle. Conventionally, DIPE is recovered by distillation and/or extraction of the fractionator bottom stream. This recovery system also separates an IPA stream and a water stream. The IPA stream can be recycled to the etherification zone.

The operating conditions of the olefin hydration and etherification process include a temperature from about 60° to 450° C., preferably from about 130° to about 220° C. and most preferably from about 150° to about 200° C., a pressure of from about 100 (700 kPa) to about 3500 psi (24,500 kPa), preferably from about 500 (3500 kPa) to about 2000 psi (14,000 kPa), a water to olefin mole ratio of from about 0.1 to about 30, preferably from about 0.2 to about 15 and most preferably from about 0.3 to about 3.

The olefin hydration process can be carried out under dense phase, liquid phase, vapor phase or mixed vapor-liquid phase conditions in batch or continuous manner, preferably using a fixed bed reactor. A liquid hourly space velocity (LHSV) of from about 0.1 to about 20, preferably about 0.1-2, when operating continuously is suitable.

The catalyst employed in the olefin hydration and etherification operations is acidic resin catalyst such as sulfonated polystyrene. Also, shape-selective acidic zeolite catalyst can be used. In general, the useful catalysts include zeolites Y, Beta, ZSM-35 and MCM-22. MCM-22 is described in U.S. Pat. No. 4,954,325 to Rubin, et al., incorporated herein by reference. Preferred catalysts include zeolite Beta and ZSM-35.

ZSM-35 is more particularly described in U.S. Pat. 4,016,245, the entire contents of which are incorporated herein by reference.

Zeolite Beta is described in U.S. Pat. No. 28,341 (of original U.S. Pat. No. 3,308,069), to which reference is made for details of this catalyst.

Zeolite Y is described in U.S. Pat. No. 3,130,007, to which reference is made for details of this catalyst.

The conventional DIPE process includes at least five main vessels comprising DIPE reactor, a $C_3$ hydrocarbon splitter, a fractionating column for the DIPE reactor effluent, an aqueous extractor vessel and a fractionator for the aqueous isopropanol phase from the extraction vessel. A hydrocarbon feedstream, typically containing propane and rich in propene is washed in a water wash tower and passed 103 to the $C_3$ splitter in conjunction with a $C_3$ recycle stream from the fractionator. Propane is removed as a bottom stream while propene is recovered as an overhead stream 106 which is condensed, accumulated and pumped to the fixed bed DIPE reactor. The feedstream to the DIPE reactor also includes isopropanol and water comprising a recycle stream recovered as an overhead from the fractionator.

Following hydration of propene to IPA and etherification in contact with acidic catalyst, under conditions described hereinbefore, the reactor effluent is introduced to the fractionator. Separation of light hydrocarbons, DIPE, IPA and water is achieved in the fractionator. The light hydrocarbons are separated as an overhead stream which is condensed to provide a liquid $C_3$ recycle stream and a $C_2$ purge stream. The fractionator bottom stream comprising DIPE, IPA, oligomers and water is subjected to aqueous extraction. Wet DIPE product is recovered as an organic phase while IPA is separated as an aqueous phase. The aqueous phase is introduced to the IPA stripper and IPA is separated, preferably as an azeotrope with water as an overhead stream, subsequently recycled to the DIPE reactor. Water is introduced to the process via the extraction step.

The incomplete conversion of propene in the DIPE reactor requires recycling $C_3$ hydrocarbons. The recycle stream must, in turn, be separated in a $C_3$ splitter in order to enrich the proportion of propene in the feed to the DIPE reactor The $C_3$ splitter represents a major part of the overall capital and operating costs of the DIPE process which, if it could be eliminated, would substantially improve overall process economics. The key to achieving this objective is the elimination of the $C_3$ recycle stream. This is accomplished in the present invention.

Referring to the FIGURE, the novel process of the present invention consists of five major vessels comprising a first stage reactor vessel 210, a second stage reactor vessel 220, fractionator 230, extractor vessel 240 and IPA-water splitter 250. The process also includes a separator 260 which may be a water wash vessel or a membrane separator.

The first and second stage reactors are distinguished from each other in that the first stage reactor contains a shape selective metallosilicate catalyst, preferably zeolite Beta. The second stage reactor preferably contains catalyst particles comprising acidic sulfonated resin, although acidic zeolite such as ZSM-5 may also be used. The second stage reactor can readily operate in the presence of large excesses of water to promote the hydration of propene to IPA along with the etherification of IPA to DIPE. Sulfonated resin catalyst has been extensively used with excess water under hydration and etherification conditions and excessive catalyst aging is not experienced. Conditions in the first reactor are intended to take advantage of the efficacy of zeolite Beta catalyst in converting IPA to DIPE while also promoting propene hydration reaction. However, it is intended that the reaction in the first reactor be primarily one of etherification. Therefore, the quantity of water in the first reactor is intentionally kept low which substantially reduces zeolite catalyst deactivation promoted by water. IPA is recycled to the first reactor instead of propene to further support etherification as the dominate reaction in the first stage reactor. This also reduces the requirements for expensive zeolite catalyst since IPA reaction with propene is much faster than propene with water. Furthermore. allows the operation of the first stage reactor at a lower pressure due to the presence of a higher concentration, of IPA in the reactor feed.

In the FIGURE, $C_3$ hydrocarbon rich in propene is passed 201 to the first stage reactor 210 in conjunction with IPA-water recycle stream 202. The effluent 203 from the first stage reactor is passed to separation zone 260 wherein the effluent is separated preferably by membrane separation or by water washing to produce a $C_3$ hydrocarbon stream 204 and a stream comprising DIPE, IPA and water 205. The $C_3$ hydrocarbon fraction 204 is introduced into the second stage fixed bed catalyst reactor unit 220 preferably in conjunction with a water feedstream 206. Preferably, the second stage reactor contains acid resin catalyst and the mol ratio of water to propene in the reactor is greater than one Hydration of propene to IPA and etherification to DIPE is carried out in the second stage reactor under conditions previously described herein for prior art DIPE process. The effluent 207 from the second stage reactor comprises unconverted $C_3$ hydrocarbons, water, IPA and DIPE which is passed to fractionator 230 in conjunction with stream 205 from separator 260. An overhead $C_3$ hydrocarbon purge stream 208 is separated in fractionator 230 as well as a bottom stream 209 comprising DIPE, IPA, and water. This bottom stream is extracted in extractor 240 with water feedstream 211 and an organic phase 212 is recovered comprising wet DIPE. An aqueous bottom phase 213 is produced comprising water and IPA which is passed to IPA splitter 250. IPA and water are recovered as an overhead stream 202 and recycled to the first stage reactor. The water fraction 214 from splitter 250 is partially recycled to extractor 240 and partially discharged with waste water stream 215.

As shown in the FIGURE by dash lines, certain optional variations can be implemented in the process. A portion of recycle stream 202 can be passed 216 to the second stage reaction zone. Also, a portion of the water feed 211 can be passed 217 to either the first stage reactor via conduit 218 or to the second stage reactor via conduit 204. Optionally, the feed to the first stage reactor can be absent water so that the reaction in that reactor is etherification. Hydration of propene is then carried out primarily in the second stage reactor. With this configuration the first stage reactor pressure can be much lower than the second stage reactor.

When referring to excess water or low water content in the first or second reactor the terms relate to the mole ratio of water to propene where excess water is that ratio of water to propene needed for complete conversion of propene, and low water content is the opposite of excess water or insufficient water to convert propene.

The above embodiment presented in the FIGURE basically illustrates a once through process for propene conversion to DIPE. The novel process eliminates the need for the $C_3$ splitter employed in prior art DIPE and also more advantageously utilizes the capabilities of zeolite catalysis for the production of DIPE.

While the invention has been described by reference to specific embodiments there is no intent to limit the scope of the invention except to describe in the following claims.

What is claimed is:

1. A process for the production of high octane value diisopropyl ether without recycling unconverted propene, comprising;
   a) contacting $C_3$ hydrocarbon feedstock containing propene and a recycle stream comprising isopropanol and water with acidic shape selective metallosilicate catalyst particles in a first reactor under olefin hydration and etherification conditions whereby a first reactor effluent stream is produced comprising diisopropyl ether, isopropanol, unconverted propene and water;
   b) separating step (a) effluent stream and recovering a first fraction comprising said unconverted propene and a second fraction comprising said diisopropyl ether and isopropanol;
   c) introducing step (b) first fraction and excess water into a second reactor under olefin hydration and/or etherification conditions in contact with acidic etherification and/or hydration catalyst particles whereby a second reactor effluent stream is produced comprising diisopropyl ether, isopropanol, unconverted $C_3$ hydrocarbons and water;
   d) separating step (b) second fraction and said second reactor effluent stream whereby a stream comprising said high octane diisopropyl ether and a stream comprising step (a) recycle stream are produced.

2. The process of claim 1 wherein step (a) metallosilicate catalyst comprises acidic zeolite.

3. The process of claim 2 wherein said acidic zeolite comprises zeolite Beta.

4. The process of claim 1 wherein step (c) catalyst particles comprise acidic resin, zeolite Beta or ZSM-35.

5. The process of claim 4 wherein said acidic resin comprises sulfonated polystyrene.

6. The process of claim 1 wherein step (a) effluent stream is separated in contact with a membrane separator to provide said first and second fractions of step (b).

7. The process of claim 1 wherein step (a) effluent stream is separated by water washing to provide said first and second fractions of step (b).

8. The process of claim 1 wherein step (d) separation process comprises the steps of:
  (e) passing step (c) effluent stream and step (b) second fraction to a stripper whereby an overhead stream comprising $C_3$ hydrocarbons and a bottom stream comprising diisopropyl ether, isopropanol and water are produced;
  (f) extracting step (e) bottom stream with water and recovering an organic phase comprising diisopropyl ether and an aqueous phase comprising isopropanol;
  (g) fractionating step (f) aqueous phase and recovering an overhead stream comprising step (a) recycle stream and a bottom stream comprising water.

9. The process of claim 8 including the further step of passing a portion of step (g) overhead stream to said second reactor.

10. The process of claim 1 further comprising introducing a supplemental feedstream comprising fresh water into said first reactor.

11. In the process for the production of diisopropyl ether comprising contacting a $C_3$ hydrocarbon feedstock containing propene and fresh water with shape selective metallosilicate catalyst particles in at least one fixed bed reactor under olefin hydration and etherification conditions, the improvement comprising;
  contacting said propene sequentially in a first reactor containing said metallosilicate catalyst under olefin hydration and etherification conditions with a recycle stream comprising isopropanol; separating said first reactor effluent and contacting unconverted propene from said first reactor with excess water in a second reactor containing acidic olefin hydration and/or etherification catalyst under olefin hydration and/or etherification conditions; and separating effluent from said first and second reactor to recover diisopropyl ether and provide said recycle stream.

12. The process of claim 11 wherein said metallosilicate catalyst comprises acidic zeolite.

13. The process of claim 12 wherein said acidic zeolite comprises zeolite Beta.

14. The process of claim 11 wherein said second reactor, catalyst particles comprise acidic resin, zeolite Beta or ZSM-35.

15. The process of claim 14 wherein said acidic resin comprises sulfonated polystyrene.

16. A process for the production of high octane value diisopropyl ether, comprising;
  a) contacting $C_3$ hydrocarbon feedstock containing propene and a recycle stream comprising isopropanol with acidic shape selective metallosilicate catalyst particles in a first fixed bed reactor under olefin etherification conditions whereby a first reactor effluent stream is produced comprising diisopropyl ether, isopropanol, unconverted propene and water;
  b) separating step (a) effluent stream and recovering a first fraction comprising said unconverted propene and a second fraction comprising said diisopropyl ether and isopropanol;
  c) introducing step (b) first fraction and excess water into a second fixed bed reactor under olefin hydration and/or etherification conditions in contact with acidic sulfonated resin etherification and hydration catalyst particles whereby a second reactor effluent stream is produced comprising diisopropyl ether, isopropanol, unconverted $C_3$ hydrocarbons and water;
  (d) passing step (c) effluent stream and step (b) second fraction to a splitter or fractionator whereby an overhead stream comprising $C_3$ hydrocarbons and a bottom stream comprising diisopropyl ether, isopropanol and water are produced;
  (e) extracting step (d) bottom stream with water and recovering an organic phase comprising diisopropyl ether and an aqueous phase comprising isopropanol;
  (f) fractionating or splitting step (e) aqueous phase and recovering an overhead stream comprising step (a) recycle stream and a bottom stream comprising water.

17. The process of claim 16 wherein said metallosilicate catalyst comprises acidic zeolite Beta.

18. The process of claim 16 wherein step (a) effluent stream is separated in contact with a membrane separator to provide said first and second fractions of step (b).

19. The process of claim 16 wherein step (a) effluent stream is separated by water washing to provide said first and second fractions of step (b).

20. The process of claim 16 including the further step of adding water to said first reactor in combination with said propene and recycle stream.

* * * * *